(12) United States Patent
Lerat et al.

(10) Patent No.: US 7,323,614 B2
(45) Date of Patent: Jan. 29, 2008

(54) DRESSING AND ANTISEPTIC AGENT CONTAINING SILVER

(75) Inventors: Yannick J. Lerat, Chalon-sur-Saône (FR); Olivier J. Poncelet, Chalon-sur-Saône (FR)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/502,684

(22) Filed: Aug. 11, 2006

(65) Prior Publication Data

US 2007/0055194 A1    Mar. 8, 2007

(30) Foreign Application Priority Data

Aug. 11, 2005 (FR) .................................. 05 08508

(51) Int. Cl.
*A61F 13/00* (2006.01)

(52) U.S. Cl. .................. 602/48; 602/41; 602/43; 602/52; 604/304; 604/307; 424/443; 424/447

(58) Field of Classification Search ............ 602/41–43, 602/48; 424/443–449; 604/304–308
See application file for complete search history.

(56) References Cited

U.S. PATENT DOCUMENTS

| 3,128,922 A | * | 4/1964 | Kuster .................. 222/389 |
| 4,728,323 A | | 3/1988 | Matson |
| 4,775,585 A | | 10/1988 | Hagiwara et al. |
| 5,470,585 A | | 11/1995 | Gilchrist |
| 5,556,699 A | | 9/1996 | Niira et al. |
| 5,888,711 A | | 3/1999 | Poncelet et al. |
| 6,027,702 A | | 2/2000 | Poncelet et al. |
| 6,620,397 B2 | | 9/2003 | Wettling et al. |
| 2005/0037058 A1 | | 2/2005 | Canada et al. |
| 2005/0115462 A1 | * | 6/2005 | Disalvo et al. ............. 106/403 |

FOREIGN PATENT DOCUMENTS

| WO | WO2004/009494 | 1/2004 |
| WO | WO2004/039724 | 5/2004 |

OTHER PUBLICATIONS

Yoshinobu Matsumura; "Presence Of Antimicrobial Agents—Topics Of Inorganic Disinfectants"; Bioscience And Industry; 2002; vol. 60; Issue 2; pp. 89-94 (English Abstract Attached).

* cited by examiner

*Primary Examiner*—Kim M Lewis

(57) ABSTRACT

The invention relates to a dressing or bandage comprising a dispersion of at least one transition metal in an imogolite or allophane matrix. In particular, it is intended for the manufacture of transparent dressings.

17 Claims, 3 Drawing Sheets

DRESSING AND ANTISEPTIC AGENT CONTAINING SILVER

FIELD OF THE INVENTION

The present invention relates to an antiseptic agent and dressings with an antiseptic agent using a transition metal, and in particular silver.

The invention has applications in the manufacture of products useable for wound care, wound protection, and the fight against the growth of micro organisms in wounds.

BACKGROUND OF THE INVENTION

The use of silver in products or dressings for wound care has been known for a long time. One knows especially of dressings in the form of bandages or compresses for local application, of which all or part is impregnated with a compound capable of delivering silver ions to the wound. Silver is thus used as an antimicrobial agent. The action of the silver can be completed by anti-odorants or humidity regulators. Silver dressings are available today in a wide variety of forms, common to modern wound care products. That is, the dressing or bandage can be a fabric structure employing woven or non-woven fiber layers (such as Smith & Nephew Acticoat or Johnson & Johnson's Actisorb), or a polymer thin film sheet, or a foam pad, or an absorptive filler dressing (such as Convatec Aquacel AG). Likewise, the silver ions can be delivered in various forms, via metallic silver, silver nano-particles, silver zeolite, silver chloride, etc. Typical dressings are multi-layer structures, with different properties relative t absorbency, moisture vapor transmission, oxygen transmission, bacterial and water barrier functionality, adhesion, and other factors, provided in the different layers. The layers are used for the physical properties that their structure provides, or serve as reservoirs of chemicals.

Various compounds containing silver ions can be used to fight against wound contamination. For example, resins incorporating silver, such as zeolites, can be used in wound dressings, as described in U.S. Pat. No. 4,775,585. Other compounds based on glass or other compounds such as carbon fibers or cellulose polymers can be used. These are for example resins, zeolites, compounds based on glass or other compounds such as carbon fibers or cellulose polymers. These compounds are capable of delivering the silver in a controlled way, and spreading it on the wound.

Various modern wound dressings are available today that provide transparency to the wound site, so that the wound can be visually inspected without direct contact by the clinician. For this reason, transparent polymer thin film dressings are frequently used, either for dry wounds or lightly exuding wounds, or as a secondary dressing, as appropriate. As an example, visual wound inspection allows the clinician to monitor wound development, including regular measurement of their dimensions, and in particular their circumference. Otherwise, these measurements, mostly made using a tape measure, can only be taken by releasing the wound from its dressings. This operation is made delicate by the fact that the wound is then unprotected.

Among the numerous silver dressings presently offered, the Arglaes Film Dressing is the only one marketed with optical transparency as an attribute. The dressing utilizes a technology described in U.S. Pat. No. 5,470,585 which incorporates the silver into a water-soluble glass. This glass, which comprises a furnace-fused complex of calcium and sodium phosphates including a silver-salt, was principally designed to provides a slow-release of silver ions, enabling a dressing to have anti-bacterial properties over an extended time period of up to a week. Optical transparency is a secondary attribute of this dressing, which can degrade during use, as the silver reacts to light and turns gray.

Dressing or bandage transparency could be useful for enabling light therapy treatment of a wound without causing undue disruption of the wound site. Subjecting wounds to light and in particular to light in the red and/or near-infrared spectrum is indeed known as a way of accelerating the healing of wounds. Light has a stimulating action on the metabolism of cells in damaged tissues inside the wound and so favors their repair. This has the effect of accelerating healing and even of repairing chronic wounds where conventional treatments are ineffective. For information one can refer to "Primary and secondary mechanisms of action of visible to near-IR radiation on cells" of Tiina Karu in J. Photochem. Photobiol. B: Biol 49 (1999), pages 1-17.

There is then a need for an improved silver dressing or bandage that provides improved optical transmission, including in the near infrared spectra, as well as improved anti-bacterial efficacy.

Other background art can be found in: US 2005/0037058; WO2004/039724; WO2004/009494; "Current trend using antimicrobial agents-Topics related to inorganic disinfectants" by Yoshinobu Matsumura in Bioscience and Industry, vol 60(2), 89-94 (2002); U.S. Pat. No. 4,728,323; U.S. Pat. No. 5,556,699; U.S. Pat. No. 5,888,711; U.S. Pat. No. 6,027,702; and U.S. Pat. No. 6,620,397.

In the context described above, the invention highlights a need to have transparent dressings. It also highlights a technical incompatibility of this need with the use of effective metal-based antimicrobial agents.

Transparency of the dressing is sought to be able to observe the wound and measure it, without having to remove the dressing. This facilitates monitoring of the wound's development. Furthermore, transparency enables the wound to be subjected to light radiation treatment, still without removing the dressing.

The property of transparency however is generally incompatible with the use of known silver-based antimicrobial agents. Indeed, silver-based compounds have insufficient transparency at thicknesses useful for viewing or irradiating wounds. Blackening of the silver, either by light activity or chemical reaction with the tissue, during the use of the dressings, can further reduce the transparency. For example, silver chloride and silver nitrate, are optically active silver forms, that change their transparency upon exposure to light.

SUMMARY OF THE INVENTION

It is the object of the invention to propose dressings that do not have the above-mentioned limitations.

One object is in particular to propose a transparent dressing enabling the wound to be measured reliably or to be subjected to light radiation without removing the dressing.

Another object is to propose a metal-based antiseptic agent compatible with the requirements of transparency.

Yet another object is to propose an antiseptic agent whose antiseptic efficiency is improved compared with the silver-based agents generally used.

To achieve these goals, the object of the invention is more precisely the use of a dispersion of a transition metal in an imogolite and/or allophone-like matrix as antiseptic agent in a dressing or bandage, i.e. for obtaining medicines intended in particular for treating microbial growth in wounds.

Also, the invention relates to apparatus and methods for applying an antiseptic agent comprising a dispersion of at least one transition metal in an imogolite and/or allophane-like matrix.

DETAILED DESCRIPTION OF THE INVENTION

Figure 1:
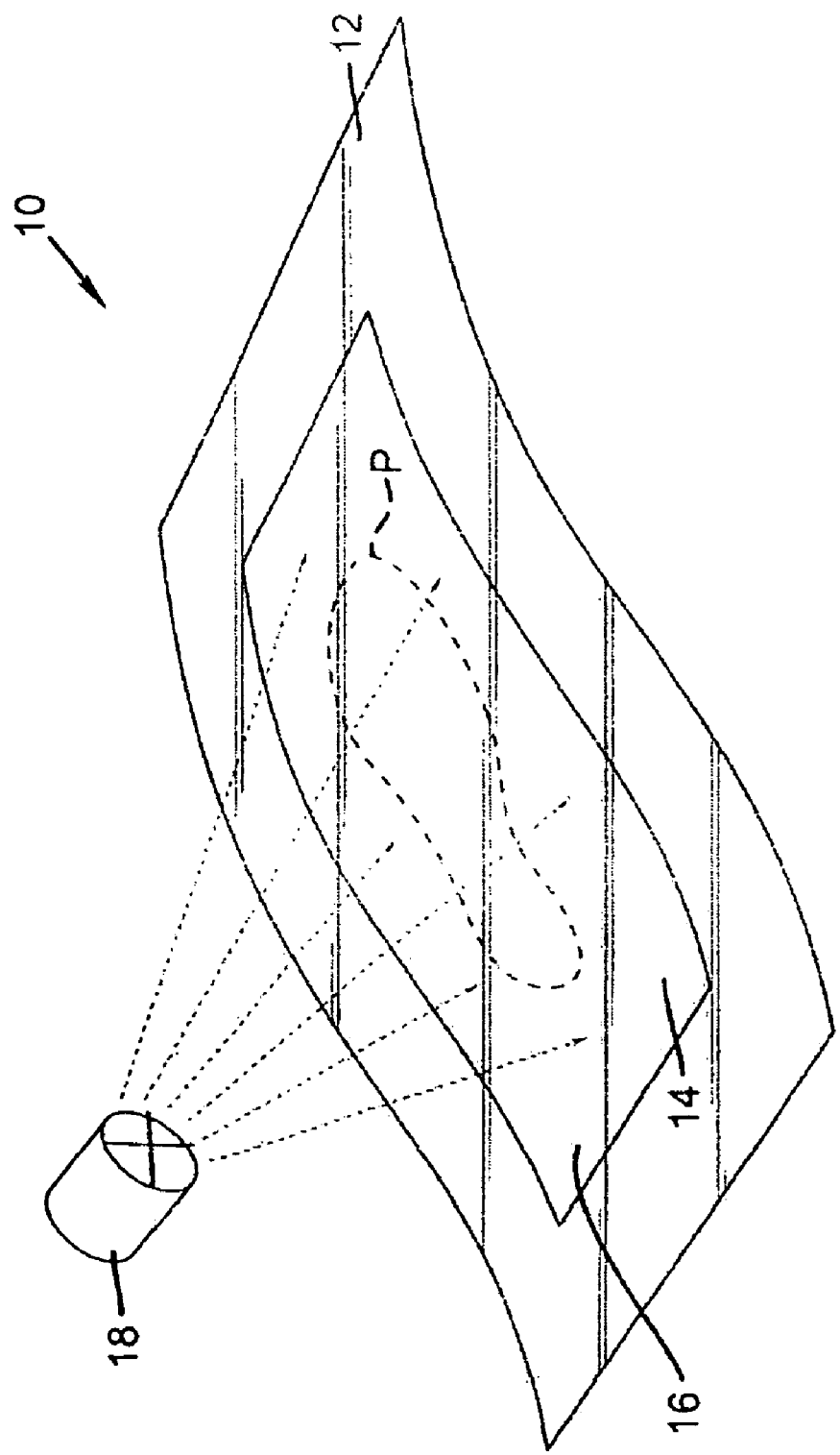
FIG. 1 illustrates a first type of dressing according to the invention.

Antiseptic agent is defined here as a substance that, at ambient temperature, enables micro-organisms to be destroyed or inhibited, and in particular bacteria, viruses or fungi found on living tissues.

An "imogolite-like" matrix means a matrix based on crystallized aluminosilicate polymers with tubular shape that can be used to form colloidal dispersions and to form films on surfaces. Imogolites and their manufacturing process are known. Their fibrous structure has the general formula $Al_xSi_yO_z$ where x:y is 1.5-2.5 and z is 2-6. The formula can also comprise an element Al and an element M selected from among Si, Ti and Zr and take the form $Al_xM_{y1}Si_{y2}O_z$ where x=0.8-3, y1=stoichiometry of M, y2=stoichiometry of Si, and z, y1 and y2 so that x/y1+y2=0.8-3, z being the fraction required for neutrality. It may be useful to refer to U.S. Pat. No. 5,888,711 and U.S. Pat. No. 6,027,702, the disclosures of which are incorporated by reference herein.

"Allophane-like" matrix means a matrix of spherical particles of an aluminosilicate-like material with a diameter of about 5 nm. It can be obtained by the reaction of an aluminum halide with an orthosilicate alkyl hydrolysable by an alkaline solution in the presence of silanol groups coming from glass or silica.

Non-hydrolysable organic groups can be also synthesized. The manufacture of allophanes or hybrid allophanes is also known. It is illustrated by U.S. Pat. No. 5,888,711 and U.S. Pat. No. 6,027,702, the disclosures of which are incorporated by reference herein.

To realize an antiseptic agent, one or several transition metals can be used. In particular, a metal selected from among Al, Ni, Fe, Cu, Zn, or Ti can be dispersed in an imogolite or allophane-like matrix by forming a gel.

To prepare the dispersion, the metal can be used in ionic form, i.e. a compound. Thus it is possible to prepare the dispersion by using silver nitrate or zinc oxide, for example. Preferably, however, the metal is used as metal powder. For example, a powder of silver, iron nickel, zinc, iron, copper or titanium is used.

In a preferred embodiment silver is used, and in particular particles of silver metal dispersed in an aqueous solution of an inorganic aluminosilicate polymer of the type mentioned. For example, this can be silver powder whose particles, with a diameter less than or equal to 10 micrometers, form a colloid in the aluminosilicate solution.

The preparation of such a dispersion is known. It may be useful in this matter to refer to U.S. Pat. No. 6,620,397, the disclosure of which is incorporated by reference herein.

The content in metal or metal compound is preferably between 5 and 10 percent by weight of the content of imogolite or allophane (Al+Si).

A metal dispersion according to the invention appears to have properties that enable the technical problems mentioned to be effectively solved and offer considerable advantages in the manufacture of dressings.

Furthermore, by adjusting the potential Hydrogen (pH) of the dispersion, its viscosity can be widely modified. For fiber structure or compress, low viscosity enables fiber impregnation in the aqueous phase.

Low viscosity, close to that of liquid water, also enables application of the antiseptic dispersion by spraying on the wound. Contact of the dispersion with the skin, salts, sweat, lymph or blood decreases its pH and considerably increases its viscosity, to the point of forming an elastic film that adheres to the wound and which can be removed later by peeling.

Another interesting property is linked to the fact that, in its use to impregnate compress, or to form a film of autonomous dressing, the described dispersion is transparent enough not only to allow treatment of the wound by light, but also for wound development to be monitored, without removing the dressing. Moreover, no blackening upon light activity or chemical reaction does occur, so that transparency is preserved.

An additional advantage of the antiseptic agent is its largely improved antiseptic efficiency, compared with other silver-based antiseptic compounds. As an illustration, a comparative test was carried out with silver-based compounds, according to the invention, and another aluminosilicate, such as zeolite, for example, that is not part of the invention.

The microbiological test is described below. This is a quantitative test adapted from the standardized methods AFNOR XP G39010:99, ASTM-E2180:01 and JIS-Z2801.

Antiseptic agents according to the invention, in this case silver dispersions in an imogolite gel and in an allophane gel were added to flasks containing a culture medium. The culture medium was a standard Trypcase Soy medium in TSB type broth (Biomérieux) that was diluted to $\frac{1}{10}$ with sterile demineralized water.

Three solutions were prepared containing 1 $cm^3$ of culture medium and a silver dispersion in an imogolite gel (1 g, 0.1 g and 0.01 g) whose final quantities of silver metal were 12 µg, 1.2 µg and 0.12 µg respectively, i.e. concentrations of 12, 1.2 and 0.12 mg/l respectively. A solution of the same type was prepared with a silver dispersion in an allophane gel.

The preparations were inoculated with 1,000,000 cells/ml of *Escherichia coli*. This is a bacterium representative of the gram-negative bacteria that are commonly found in wounds. The solutions were incubated at 37° C. for three days. Every day, the number of bacteria was counted on an aliquot of the incubated solutions, using the box counting method with Trypcase Soy agar medium of TSA type (Biomérieux).

In the same way, a culture medium was prepared containing 1 $cm^2$ of a textile with density 14 mg/$cm^2$, soaked with a known antiseptic based on a silver compound and zeolite with silver content of 500 µg/g. The quantity of silver introduced by the fabric was thus 7 µg, i.e. a maximal potential concentration of 7 mg/l, if all the silver is dispersed from the fabric to the solution.

The samples were inoculated in the way described and incubated at 37° C.

Table I below summarizes the results observed after 24 hours, 48 hours and 72 hours respectively. Samples with an imogolite base are marked "Imo", the sample with allophane base is marked "Allo" and the sample with zeolite base is marked "Zeo".

TABLE I

| Sample | Silver quantity | Bacteria per ml after 24 hr | Bacteria per ml after 48 hr | Bacteria per ml after 72 hr |
|---|---|---|---|---|
| Imo 1 | 12 µg | 0 | 0 | 0 |
| Imo 2 | 1.2 µg | 0 | 0 | 0 |
| Imo 3 | 0.12 µg | 0 | 0 | 0 |
| Allo | 1 µg | 0 | 0 | 0 |
| Zeo | 7 µg | $>5 \cdot 10^8$ | $>5 \cdot 10^8$ | $>5 \cdot 10^8$ |

The table shows a very strong antibacterial action of an antiseptic according to the invention. This result was not obtained with a known silver-based compound and an aluminosilicate compound such as zeolite.

In the very strict operating conditions described, it may be seen that the distribution of silver from the zeolite-based compound was insufficient to prevent bacterial proliferation. This results is consistent with article (8) that indicates a minimum inhibiting concentration above which *E. coli* no longer develops, at around 62.5 mg/l for a known silver-based compound and an aluminosilicate compound such as zeolite. In the test related to table I, this material could not generate better than 7 mg/l of silver, which explains its ineffectiveness in the conditions described.

Another comparative test was carried out between various antiseptic agents according to the invention, prepared with the metals Ag, Cu and Zn, respectively. The protocol used was the same as that described above. For each sample, 1 g of solution was used in the test. A control sample was prepared by adding 1 gram of metal-free imogolite to the culture medium.

Table II below gives the count of *Escherichia coli* bacteria made for each inoculated sample after 24 hours, 48 hours and 72 hours, respectively. The samples are marked "IMO test" for the control sample, and IMO followed by the symbol of the transition metal used for the other samples.

It may be seen that the antibacterial action is very strong for each of the antiseptic agents and does not depend on a particular choice of transition metal.

TABLE II

| *Escherichia coli* 37° C. | Bac./ml 24 H | Bac./ml 48 H | Bac./ml 72 H |
|---|---|---|---|
| IMO test | >500 000 000 | >500 000 000 | >500 000 000 |
| IMO + Ag | 0 | 0 | 0 |
| IMO + Cu | 0 | 0 | 0 |
| IMO + Zn | 0 | 0 | 0 |

The results of a comparable analysis are given in the table III. The test was carried out according to an identical process, with the exception that the samples were inoculated with the bacterium *Staphylococcus hominis* which is a gram-positive bacterium very common in wounds. Despite slower bacterial growth seen on the control sample, the bactericidal action of the antiseptic agents according to the invention was again observed.

TABLE III

| *Staphylococcus hominis* 37° C. | Bac./ml 24 H | Bac./ml 48 H | Bac./ml 72 H |
|---|---|---|---|
| IMO test | 1 300 000 | 1 600 000 | 2 400 000 |
| IMO + Ag | 0 | 0 | 0 |
| IMO + Cu | 0 | 0 | 0 |
| IMO + Zn | 0 | 0 | 0 |

Table IV below illustrates the fungicidal action of the antiseptic agents according to the invention. Following the same experimental process, the samples were then inoculated with a yeast, in this case *Candida albicans*.

A strong fungicidal action was observed. More prolonged action seemed to exist for antiseptics prepared based on copper and zinc.

TABLE IV

| *Candida albicans* 37° C. | Bac./ml 24 H | Bac./ml 48 H | Bac./ml 72 H |
|---|---|---|---|
| IMO test | 150 000 | 400 000 | 900 000 |
| IMO + Ag | 0 | 80 | 1000 |
| IMO + Cu | 0 | 0 | 0 |
| IMO + Zn | 0 | 0 | 0 |

Other characteristics and advantages of the invention will appear in the following description, with reference to the figures of the appended drawings. This description is given purely as an illustration, and is not limiting.

The dressing 10 of FIG. 1 has a support structure 12, which for example, can be in the in the form of a fabric, with woven or non-woven fibers. As another example, support structure 12 could be a transparent film, made for example, from a polymer such as a non-toxic polyurethane. The properties of structure 12, which may have a single layer or multi-layer design, will be determined relative to the required abilities to prevent water and bacterial penetration, while providing some degree of moisture vapour and oxygen transfer, and perhaps, moisture absorbency.

As one example, the dressing 10 could be fabricated with antiseptic agent of the present invention applied to the structure 12 in entirety, which could comprise a hydrofiber, such that dressing 10 could be placed into a cavity type wound, to enhance internal healing. As an alternative, a multi-layer dressing, comprising at least a polymer membrane (polyurethane) with antiseptic agent and foam layer could be constructed. This dressing could also be used for cavity type wounds, with the polyurethane membrane in contact with the wound tissue, and the accompanying foam layer present to absorb exudates that pass through the membrane. Although the transparency advantages of the dressings of the present invention may be reduced when used in an internal cavity dressing, the advantageous antibacterial efficacies are still applicable. Bandage structure 12 may also provide a surrounding zone with an adhesive means capable of being put in contact with the healthy skin around a wound P to hold the dressing on the wound. Such an adhesive would be selected relative to its ability to adhere to tissue while minimizing tissue damage and pain upon removal, while acting as a bacterial barrier that allows controlled moisture vapor transfer.

In a central zone 14 capable of being put in contact with a wound P, the dressing includes an antiseptic agent according to the invention. For example, the antiseptic agent can possibly soak into a layer of fibers 16 forming a compress. The antiseptic agent, can be applied to a foam or hydrophilic fibrous structure (absorbent filler) primary dressing, which is in contact with, or integrated with, a fabric or film based secondary dressing. The antiseptic agent could also be coated directly onto the inner surface of a polymer film (such as a polyurethane). The antiseptic agent can also be comprised of a layer of a dispersion according to the invention in gel form, with sufficient viscosity to ensure its own cohesion. It can also impregnate the whole dressing.

The central zone 14 has the special feature of being transparent. It coincides, for example, with a nominally transparent region in the support structure 12. Transparency is obtained thanks to the transparent property of the silver dispersions of the invention used in combination with the generally transparent properties of the other bandage structures. For example, many thin polymer films, such as polyurethane, are nominally transparent, and could provide a support surface for the antiseptic agent. In the case of a fabric dressing, the fibers may be provided in a sufficiently loose mesh to be effectively transparent, or may incorporate a nominally transparent fiber in combination with fibers that may have minimal transparency. The transparency of the zone in contact with the wound, or by extension the whole dressing, is also described later in connection with FIG. 3. It enables the development of the size and the condition of the wound P to be monitored and enables it to be subjected to the action of light, coming from a source schematically shown by reference 18 of FIG. 1.

It is noted that the transparency goals for wound monitoring and light therapy may be different. For visual wound inspection, by eye or with a camera, a high optical transmission with minimum light scattering and diffraction is preferred, such that clear images can be obtained. In the case of light therapy, a greater degree of light scattering and diffraction might be tolerated as the light is being delivered to the tissue for treatment purposes, rather than for imaging. Light therapy can be applied with visible light, bit most commonly uses red and near infrared light, between ~600-1300 nm. In such cases, unlike laser surgery for example, the light generally can be applied to the tissue broadly, rather than with the spatial resolution and precision required in imaging or laser surgery. In general, dressing transparency >70% is desirable, although lower values could be acceptable.

The dressing of FIG. 1 has been described in multiple potential forms, potentially including woven or non-woven fabrics, polymer membranes, foams, hydrofibers, and other dressing materials and constructions. As wounds can be complex, and occur in a multitude of conditions, there exists a spectrum of wound care dressings. Not only are there the common acute wounds (small scratches and cuts), but surgical wounds, chronic wounds (pressure ulcers, venous stasis ulcers, diabetic ulcers, etc.), and burns, many of which may require the use of one or more types of dressings during the wound healing. In general, the transition metal imogolite or allaphone-like matrix compounds of the present invention are considered to be applicable and efficacious as components within many types of wound dressings.

Figure 2:
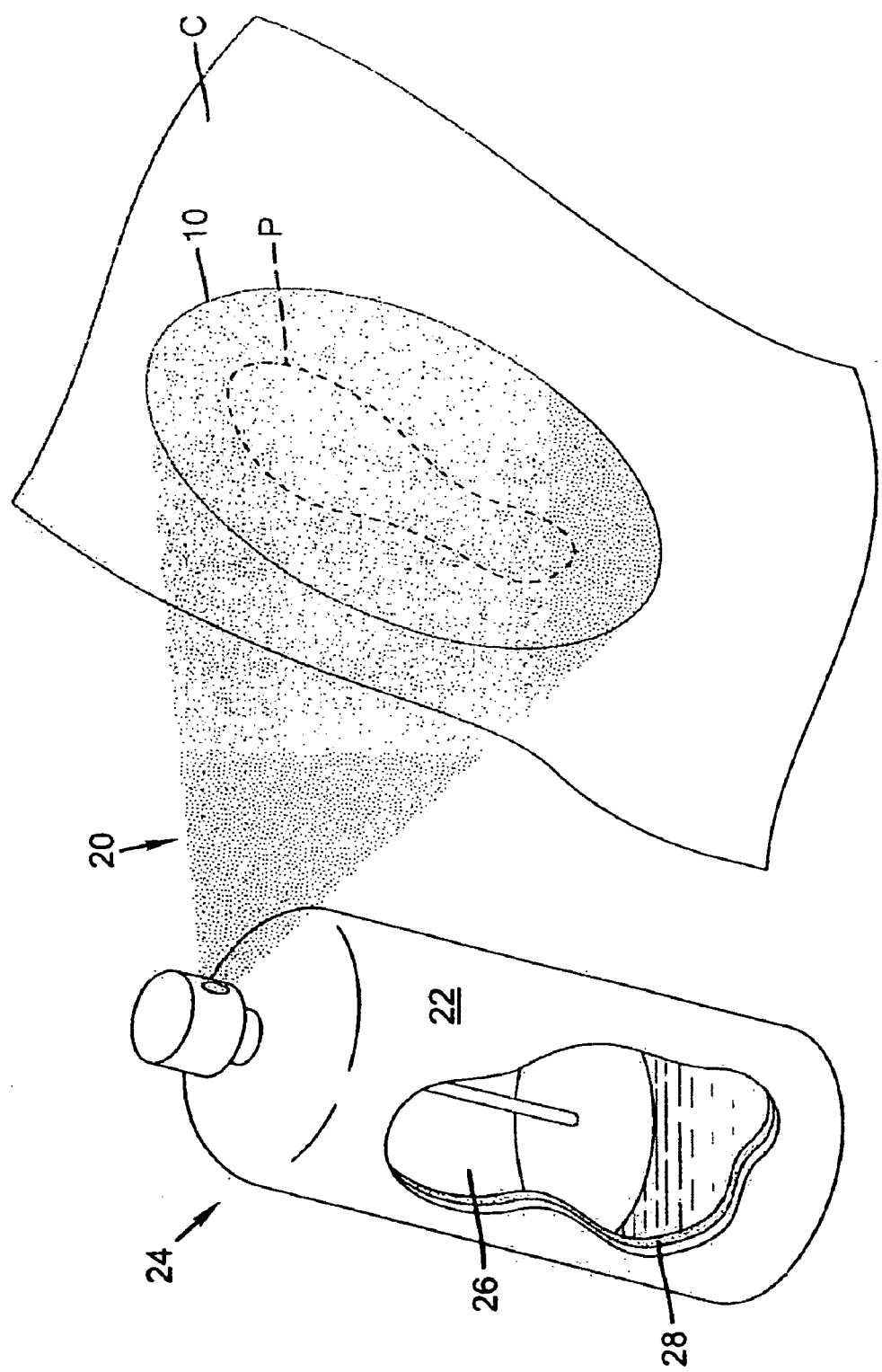
FIG. 2 illustrates a second type of dressing according to the invention.

FIG. 2 shows another form of dressing and another method of application of the dressing. The dressing is comprised of the dispersion directly, i.e. by the antiseptic agent.

The dressing 10 is formed by spraying a dispersion 20, according to the invention, on the skin C. The dispersion is sprayed to cover the wound P and, preferably, part of the healthy skin surrounding the wound.

The dispersion 20 is contained in the can 22 of a spray 24 shown in partial cut-away view. The dispersion whose potential Hydrogen is higher than 4.5 has low viscosity, close to that of liquid water. However, after spraying on the skin C, under the effect of the skin's acidity and the physiological liquids found there, the dispersion's viscosity increases strongly so that the dispersion is almost immediately transformed into an elastic film that constitutes the dressing. Indeed, it is found that a small variation of the dispersion's potential hydrogen strongly modifies its viscosity. The film can then later simply be peeled off.

The can of the spray also contains a driving gas 26 used to propel the dispersion. This is a gas that is inert in relation to the dispersion and in particular a gas that cannot modify the acidity. This prevents any increase of the viscosity inside the can. The propellant gas is, for example, pressurized nitrogen.

Possibly an inert coating 28 can cover the internal wall of the can to prevent interactions between the dispersion and the can material.

Figure 3:
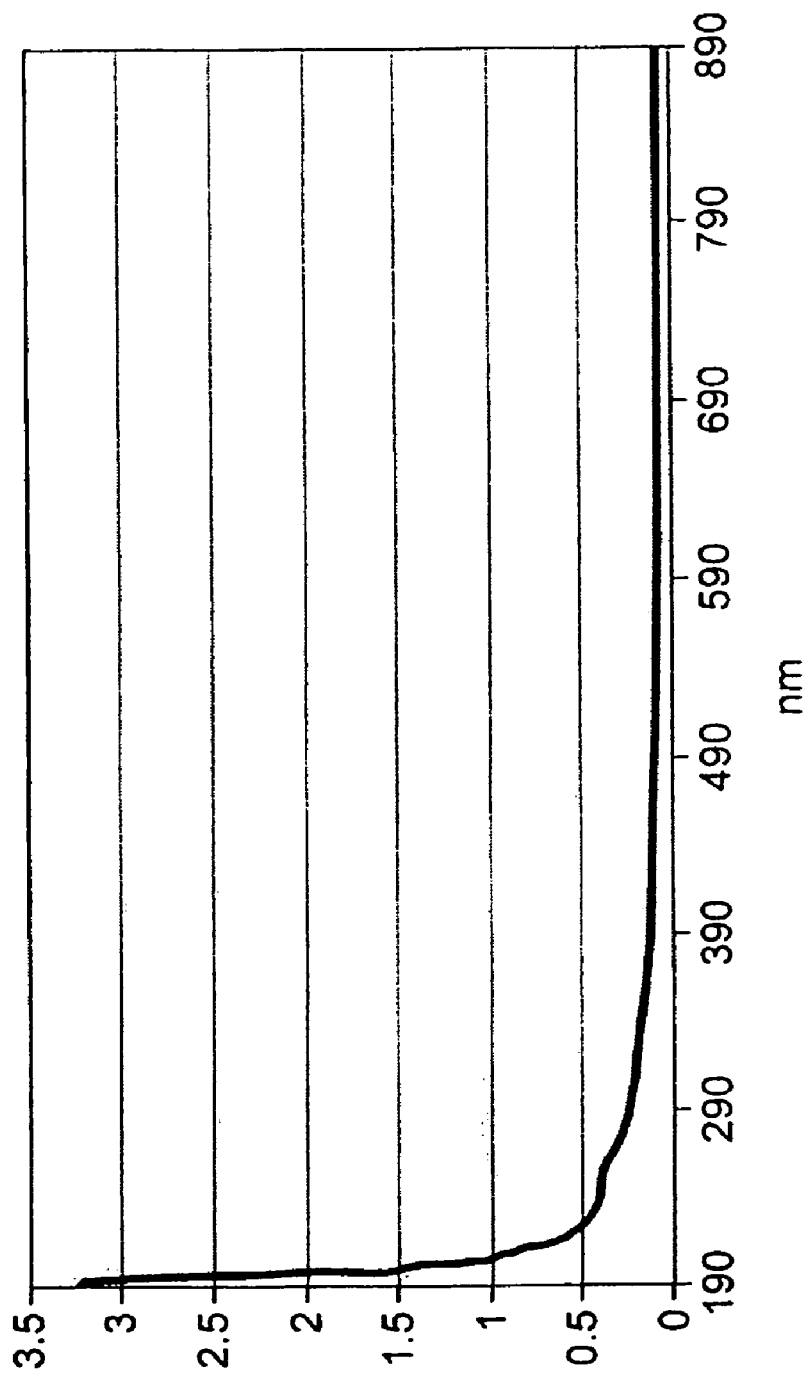
FIG. 3 is a graph illustrating a particular property of an antiseptic agent and a dressing according to the invention.

FIG. 3 is a graph illustrating the absorption spectrum of a dressing according to the invention in the form of a dispersion of silver in an imogolite matrix.

The measurements in FIG. 3 correspond to a layer of dispersion one centimeter thick, i.e. a thickness much greater than a dressing which is only about a millimeter. The transparency of a dressing is thus even better than the sample used for the measurements.

The graph plots the energy absorption expressed in Optical Density (no unit) along the ordinate against the light wavelength along the abscissa.

It may be seen that, in the visible spectrum and in the spectrum of wavelengths favorable to wound care, i.e. about 600-890 nm (red and near-IR), the absorption is very low (less than 0.5). The light absorption is also quite low throughout the green and blue portions of the visible spectrum, such that a clinician could make a full color visual inspection. The material therefore enables the wound not only to be seen but also to be subjected to light treatment.

The invention has been described in detail with particular reference to certain preferred embodiments thereof, but it will be understood that variations and modifications can be effected within the spirit and scope of the invention.

The invention claimed is:

1. A dressing or bandage comprising an antiseptic agent comprising a dispersion of at least one transition metal in an imogolite and/or allophone-like matrix, wherein the dispersion of at least one transition metal in an imogolite and/or allophone-like matrix is substantially optically transparent in the visible and the near infrared spectrum.

2. A dressing or bandage according to claim 1 wherein the dispersion comprises the metal in its metal form.

3. A dressing or bandage according to claim 1 wherein the dispersion comprises the metal in an ionic form.

4. A dressing or bandage according to claim 1 wherein the antiseptic agent comprises at least one of the following metals: Al, Ni, Cu, Zn, Ti, Fe, and Ag.

5. A dressing or bandage according to claim 4 wherein the antiseptic agent comprises a silver dispersion.

6. A dressing or bandage according to claim 1 comprising a fabric, foam, film, or absorptive filler, incorporating said antiseptic agent.

7. The dressing or bandage of claim 1 wherein said dressing or bandage provided with the dispersion is provided with a surrounding zone of adhesive capable of being put into contact with skin.

8. The dressing or bandage of claim 1 wherein the bandage or dressing is provided with a polymer transparent film.

9. The dressing or bandage of claim 8 wherein the transparent film provides moisture vapor and oxygen transfer.

10. The dressing or bandage of claim 1 further comprising fibers in a loose mesh to be effectively transparent.

11. Apparatus for applying a dressing by spraying, comprising a can with spray valve containing an antiseptic agent comprising a substantially optically transparent in the visible and the near infrared spectrum dispersion of at least one transition metal in an imogolite and/or allophane-like matrix.

12. Apparatus according to claim 11 wherein the can also contains pressurized nitrogen used as propellant.

13. An apparatus according to claim 11 wherein the dispersion comprises the metal in its metal form.

14. An apparatus according to claim 11 wherein the dispersion comprises the metal in an ionic form.

15. An apparatus according to claim 11 wherein the antiseptic agent comprises at least one of the following metals: Al, Ni, Cu, Zn, Ti, Fe, and Ag.

16. An apparatus according to claim 11 wherein the antiseptic agent comprises a silver dispersion.

17. An apparatus according to claim 11 wherein the antiseptic agent has, in the can, a pH higher than 4.5.

* * * * *